United States Patent [19]

Dourdeville

[11] Patent Number: 6,099,724
[45] Date of Patent: Aug. 8, 2000

[54] ACTIVE PUMP PHASING TO ENHANCE CHROMATOGRAPHIC REPRODUCIBILITY

[75] Inventor: Theodore A. Dourdeville, Marion, Mass.

[73] Assignee: Waters Investments Limited

[21] Appl. No.: 09/233,555

[22] Filed: Jan. 20, 1999

Related U.S. Application Data

[62] Division of application No. 08/870,661, Jun. 6, 1997, Pat. No. 5,897,781.

[51] Int. Cl.7 ................................................... B10D 15/08
[52] U.S. Cl. .................... 210/198.2; 210/656; 210/101
[58] Field of Search .................................... 210/656, 659, 210/90, 101, 198.2; 417/2, 3, 4, 5, 6, 7, 8, 26, 43, 44.2, 53

[56] References Cited

U.S. PATENT DOCUMENTS

| | | | |
|---|---|---|---|
| 3,917,531 | 11/1975 | Magnussen | 210/198.2 |
| 3,922,957 | 12/1975 | Ogle et al. | 92/137 |
| 4,032,445 | 6/1977 | Munk | 210/198.2 |
| 4,043,906 | 8/1977 | Helmer | 417/22 |
| 4,131,393 | 12/1978 | Magnussen, Jr. | 417/22 |
| 4,595,495 | 6/1986 | Yotam | 210/198.2 |
| 4,595,496 | 6/1986 | Carson | 210/101 |
| 4,767,279 | 8/1988 | Dourdeville | 210/198.2 |
| 4,883,409 | 11/1989 | Strohmeier et al. | 417/43 |
| 5,071,562 | 12/1991 | Allington et al. | 210/656 |
| 5,253,981 | 10/1993 | Yang et al. | 417/3 |
| 5,360,320 | 11/1994 | Jameson et al. | 417/4 |
| 5,393,434 | 2/1995 | Hutchins et al. | 210/656 |
| 5,608,517 | 3/1997 | Munk | 356/246 |
| 5,637,208 | 6/1997 | Dourdeville | 210/198.2 |
| 5,897,781 | 4/1999 | Dourdeville | 210/198.2 |

*Primary Examiner*—Ernest G. Therkorn
*Attorney, Agent, or Firm*—Brian Michaelis; Anthony J. Janiuk

[57] ABSTRACT

A fluid delivery method and apparatus implementing active phasing to actively restore the substantially exact mechanical positions of driven components in a delivery system in order to precisely reproduce the mechanical signature and hydraulic characteristics of the system from run to run without perturbing output flow. The delivery system is configured to intelligently drive pump pistons to a known position and to delivery fluid(s) at a known pressure, and includes a plurality of pump modules each including motor driven syringes having respective pistons configured to reciprocate under control of a control mechanism. Pump phasing is accomplished through a mechanism of compensation delivery of the syringes. An independent, motor-driven syringe of any given pump in a plurality of pumps in a system has the ability to act as a delivering syringe to maintain a prescribed output flow while one other syringe of each of the plurality of pumps is repositioned under load. With the delivering syringe maintaining output flow, the syringe which is repositioning, i.e. being phased, can substantially simultaneously arrive at a destination position and at a destination pressure.

13 Claims, 8 Drawing Sheets

| CURRENT SYNCH SYRINGE STATE | CURRENT NON-SYNCH SYRINGE STATE | AMOUNT OF TRAVEL REMAINING IN NON-SYNCH SYRINGE | SYNCH PROCESS |
|---|---|---|---|
| COMPRESS | DELIVER | ADEQATE TO PROVIDE DELIVERY PLUS REPOSITIONING VOLUME | SHORT (124) |
| COMPRESS | DELIVER | NOT ADEQUATE TO PROVIDE DELIVERY PLUS REPOSITIONING VOLUME | LONG (126) |
| DELIVER | COMPRESS | ANY | LONG (126) |
| DELIVER | DELIVER | ANY | LONG (126) |

SYSTEM IN RUN IDLE STATE

FIG. 6A

ACTIVE PUMP PHASING TO ENHANCE CHROMATOGRAPHIC REPRODUCIBILITY

The application is a division of U.S. Ser. No. 08/870,661 filed Jun. 6, 1997, now U.S. Pat. No. 5,897,781.

FIELD OF THE INVENTION

The present invention relates to liquid chromatography instrumentation and solvent delivery systems, and more particularly to a method and apparatus for the control of chromatographic pumping systems.

BACKGROUND OF THE INVENTION

High-pressure liquid chromatography (HPLC) solvent delivery systems are used to source either single-component liquids or mixtures of liquids (both known as "mobile phase") at pressures which can range from substantially atmospheric pressure to pressures on the order of ten thousand pounds per square inch. These pressures are required to force the mobile phase through the fluid passageways of a stationary phase support, where separation of dissolved analytes can occur. The stationary phase support may comprise a packed bed of particles, a membrane or collection of membranes, or an open tube. Often, analytical conditions require the mobile phase composition to change over the course of the analysis (this mode being termed "gradient elution"). In gradient elution, the viscosity of the mobile phase may change and the pressure necessary to maintain the required volumetric flow rate will change accordingly.

Other analytical conditions may require that the mobile phase composition remain fixed over time (this mode being termed "isocratic elution"). However, the fixed composition may result from the mixture of multiple components, and often the relative amounts of the components must be controlled to fractional per cent levels in order to achieve the separations goals.

In liquid chromatography, the choice of an appropriate separation strategy (including hardware, software, and chemistry, results in the separation of an injected sample mixture into its components, which elute from the column in reasonably distinct zones or "bands". As these bands pass through a detector, their presence can be monitored and a detector output (usually in the form of an electrical signal) can be produced. The pattern of analyte concentration within the eluting bands, which can be represented by means of a time-varying electrical signal, gives rise to the nomenclature of a "chromatographic peak". Peaks may be characterized with respect to their "retention time", which is the time at which the center of the band transits the detector, relative to the time of injection (i.e. time-of-injection is equal to zero). In many applications, the retention time of a peak is used to infer the identity of the eluting analyte, based upon related analyses with standards and calibrants. The retention time for a peak is strongly influenced by the mobile phase composition, and by the accumulated volume of mobile phase which has passed over the stationary phase.

The utility of chromatography relies heavily on run-to-run reproducibility, such that standards or calibrants can be analyzed in one set of runs, followed by test samples or unknowns, followed by more standards, in order that confidence can be had in the resulting data. Known pumping systems exhibit some non-ideal characteristics which result in diminished separation performance and diminished run-to-run reproducibility. Among the non-ideal pump characteristics exhibited in known pumping systems are, generally, fluctuations in solvent composition and/or fluctuations in volumetric flow rate.

Volumetric flow fluctuations present in known HPLC pumping systems disadvantageously cause retention time(s) to vary for a given analyte. That is, the amount of time that an analyte is retained in the stationary phase fluctuates undesirably as a function of the undesirable volumetric flow fluctuations. This creates difficulties in inferring the identity of a sample from the retention behavior of the components. Volumetric flow fluctuations can result in fluctuations in solvent composition when the output of multiple pumps are summed to provide a solvent composition.

Fluctuations in solvent composition present in known HPLC pumping systems can disadvantageously result in interactions with the system's analyte detector and produce perturbations which are detected as if they arose from the presence of a sample. In effect, an interference signal is generated. This interference signal is summed with the actual signal attributable to the analyte, producing errors when the quantity of an unknown sample is calculated from the area of the eluting sample peak.

The prior art is replete with techniques and instrument implementations aimed at controlling solvent delivery and minimizing perturbations in the output of delivery systems for analytical instrumentation. Myriad pump configurations are known which deliver fluid at high pressure for use in applications such as liquid chromatography. Known pumps, such as one disclosed in U.S. Pat. No. 4,883,409 ("the '409 patent") incorporate at least one plunger or piston which is reciprocated within a pump chamber into which fluid is introduced. Frequency and stroke length of the plunger reciprocating within the pump chamber is controllable to control the flow rate of fluid output from the pump. However, the assembly for driving the plunger is an elaborate combination of elements that can introduce undesirable motion in the plunger as it is driven, which motion make it difficult to precisely control delivery system output and results in what is termed "noise" or detectable perturbations in a chromatographic baseline. Much of this noise does not result from random statistical variation in the system, rather much of it is a function of a mechanical "signature" of the pump. Mechanical signature is correlated to mechanically related phenomena such as anomalies in ball and screw drives, gears, and/or other components used in the pump to effect the linear motion that drives the piston(s), or it is related to higher level processes or physical phenomena such as the onset or completion of solvent compression, or the onset of solvent delivery from a cylinder Typical systems known for delivery of liquids in liquid chromatography applications, such as disclosed in the '409 patent and further in U.S. Pat. No. 5,393,434, implement dual piston pumps having two interconnected pump heads each with a reciprocating plunger. The plungers are driven with a predetermined phase difference in order to minimize output flow variations. Piston stroke length and stroke frequency can be independently adjusted when the pistons are independently, synchronously driven. Precompression can be effected in each pump cylinder in any given pump cycle to compensate for varying fluid compressiblities in an effort to maintain a substantially constant system pressure and output flow rate.

However, in such systems known in the prior art there is no guarantee that from one piston stroke to the next, or from one chromatography run to the next, that significant physical events such as the onset or completion of fluid compression or fluid delivery, occur at precisely known pump mechanical positions. Further, in such systems known in the prior art there is no guarantee that from one piston stroke to the next, or from one chromatography run to the next, that attainment of precisely known mechanical positions occurs at prescribed and repeatably points in successive chromatographic runs.

With known delivery systems, at the termination of a chromatographic run each of the active pumps in a system can reside at a seemingly arbitrary mechanical position or phase. If a new run commences directly from an arbitrary mechanical phase, the mechanical signature of the system will differ, negatively affecting the results of the chromatographic analysis.

This is of particular relevance to the gradient mode of chromatography, where system pressure has to vary dynamically to maintain constant flow while solvent viscosity changes. The hydraulic characteristic of the system, particularly the system hydraulic capacitance, vary as a function of the pump mechanical phase. A variation in the system hydraulic capacitance will change the time-constant of the system hydraulic response. Therefore, the tracking of the delivery pressure profile, and the actual volumetric delivery, will not be precisely repeatable from run to run. Over multiple chromatographic runs, relative motion occurs between a chromatographic peak and features in the surrounding baseline which negatively affects the precision of determining peak areas and retention times, and therefore negatively affects the ability of the chromatography to quantitative the sample amount and to infer the identity of the sample.

SUMMARY OF THE INVENTION

The present invention provides a solvent delivery method and apparatus implementing active phasing to actively restore the substantially exact mechanical positions of driven components in a delivery system, without substantially perturbing the ongoing flow, in order to enhance the reproducibility of solvent delivery from run to run.

According to the invention a solvent delivery system is configured to include mechanisms that intelligently drive pump pistons to a known position and to deliver fluid(s) at a known pressure. The delivering syringes of each of the active pumps in the system are restored to a known mechanical phase prior to initiation of the next run, which maintaining the required volumetric flow rate and solvent composition delivered to the system, and while in the contest of a run all subsequent transitions or handoffs from one pump module to the next can be handled using the same set of logical steps.

The delivery system includes at least one "logical pump" including at least two pump modules each having motor driven syringes with respective pistons or plungers configured to reciprocate under control of a control mechanism such as a microprocessor controller. Pump phasing is accomplished through a mechanism of complementary or compensation delivery effected by the syringes working in synchronization. An independent, motor-driven syringe of any given pump in a plurality of pump modules comprising a logical pump in a delivery system has the ability to act as a delivering syringe complementing or maintaining a prescribed output flow to the system while one other syringe of that logical pump is repositioned under load. With the delivering syringe maintaining output flow, the syringe which is repositioning, i.e. being phased, can substantially simultaneously arrive at a destination position and at a destination pressure. The act of restoring the syringe(s) to the known phase produces substantially no perturbation to the composition or flow rate of mobile phase being continuously delivered to the receiving system.

Features of the invention include enhancement of analytic systems where solvent pumping, solvent composition gradient generation, and solvent mixing are critical to the precision, accuracy and sensitivity of the analysis, as in high performance liquid chromatography. Systems implemented according to the invention utilize the deterministic nature of the mechanical signature and hydraulic characteristics of the delivery mechanism(s), e.g. pumps, to improve the qualitative and quantitative capabilities of the chromatographic system, thus improving data integrity across multiple runs by reducing analyte retention-time variability and stabilizing pump-induced detector interference.

BRIEF DESCRIPTION OF THE DRAWING

The foregoing and other features and advantages of the present invention will be more fully understood from the following detailed description of an illustrative embodiment, taken in conjunction with the accompanying drawing in which:

FIG. 6A is a table illustrating potential initial conditions of a first and second syringe in the local pump of FIG. 1 and corresponding active phasing step flow according to a flow diagram of FIG. 6B;

DETAILED DESCRIPTION

Figure 1A:
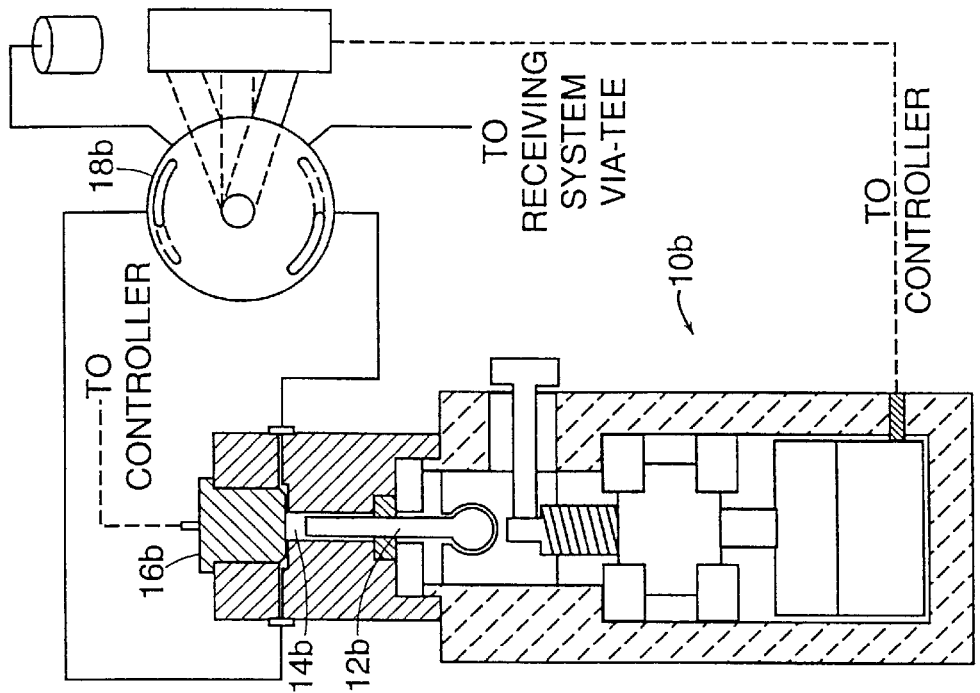
FIGS. 1A and 1B are block diagrams of a logical pump in a system implementing active pump phasing according to the invention.
Figure 1B:
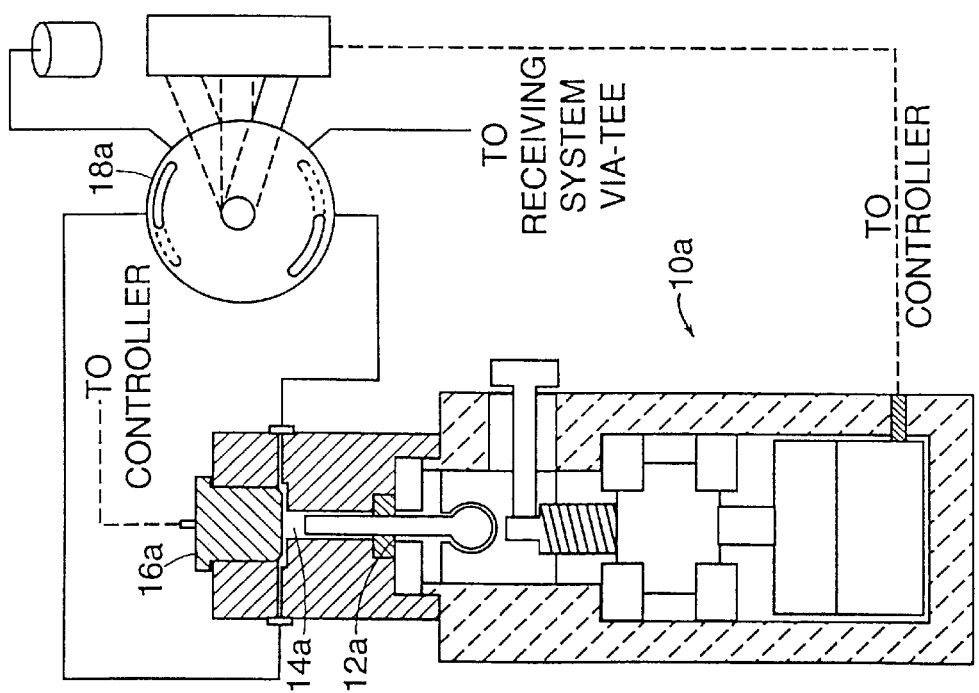

Active pump phasing according to the invention is preferably implemented in a continuous delivery system comprising at least two pumping units, such as described in detail in co-pending, commonly owned U.S. Pat. No. 5,637,208 entitled SOLVENT PUMPING SYSTEM issued Jun. 10, 1997, the entirety of which is incorporated herein by reference. Such a system is constituted by a logical pump, illustrated in FIG. 1, including two substantially identical pump modules 10a, 10b working in conjunction with each other to effect continuous delivery from the logical pup. Each of the pump modules 10a, 10b includes a syringe formed by a microstep motor driven plunger or piston 12a, 12b actuatable to drive fluid out of a respective pump chamber 14a, 14b. Each of the syringes has a dedicated pressure sensor 16a, 16b providing a respective pressure signal to a microprocessor control (not shown). Respective selector valves 18a, 18b and associated valve actuators operate under microprocessor control to effect at least three functional positions for each valve, including: "fill", "dead-ended" (i.e. isolated), and "deliver".

The delivery system, as describe in the referenced U.S. Patent, transitions through a number of discrete states to effect a complete delivery cycle. Such a system is appropriately configured for implementing active phasing according to the invention in that there is a dedicated motor for each piston, allowing decoupling of piston motion of the first piston relative to the second piston. Accordingly, solvent compressibility can be dealt with "off-line" in one pump module while the other pump module is delivering or is otherwise engaged. That is, solvent can be brought into one pump chamber at atmospheric pressure and be compressed (typically brought up to system pressure), while the associated selector valve is in the dead-ended state, independent of the operation of the other pump module. The off-line, compressed solvent can be retained at the desired pressure pending delivery, and ultimately be finely equilibrated and delivered as needed.

In the illustrative logical pump implementation describe in the referenced U.S. Patent, a selector valve is used that has no volumetric error in switching (i.e. a positively actuated zero switching volume valve), such that the new volume of liquid from the dead-ended chamber can be brought on-line with no net change in system pressure and no volumetric error in the cross over. Correspondingly, when the previously on-line syringe is taken off-line there will be no net change in system pressure and no volumetric error. The delivery system described effects continuous delivery with no system pressure charge-up transient associated with the start of every run. The pressure sensors directly in line with the respective pump head monitor off-line chamber or cylinder pressure charge-up and discharge, and are configured so that there is always at least one sensor in hydraulic continuity with the system solvent flow.

The use of individual motor for each piston, as opposed to out-of-phase-cam-single-motor pumps known in the prior art, facilitates active phasing according to the invention in that compensation delivery can be effected wherein one pump module of a logical pump can be repositioned under load to a "synch" position, while the other pump module of that logical pump is providing compensation delivery (i.e. providing negative delivery or controlled/reduced positive delivery). Accordingly, the fluid delivery out of the logical sum is not interrupted during the repositioning/synch positioning procedure. This effective cross-flow of liquid within a logical pump permits each pump module of the delivery system, and the delivery system overall, to be re-phased during operation. Such re-phasing or active phasing of the delivery system enables all chromatography runs to proceed from a know mechanical starting phase or position, and to sustain mechanical phasing during execution of a run. Accordingly, variability of solvent delivery as a function of pump mechanical phase, it substantially eliminated as a variable across chromatographic runs, enhancing run-to-run reproducibility.

As will be appreciated by those skilled in the art, chromatographic implementations may involve the pumping of several fluids by way of a corresponding number of logical pumps. Active phasing according to the invention is optimally implemented when all logical pumps in a delivery system are restored to a known mechanical position prior to initiation of the next run, and where the act of restoring the known phase produces substantially no perturbation to the composition or flow rate of mobile phase being continuously delivered to the receiving system.

Generally, active phasing is implemented as a sequence of behaviors, described in detail and illustrated hereinafter in FIGS. 2–7, with respect to a single logical pump comprised of a first pump module having as syringe designated as the syringe to be synchronized (or "synch syringe") and a substantially mechanically identical second pump module having a syringe designated as an auxiliary syringe ("nonsynch syringe"). The sequence of behaviors will vary slightly (i.e. is longer or shorter requiring greater or fewer mechanical phase) depending upon a "snapshot" of the pump mechanical phase when a command is issued to undertake active phasing. That is, active phasing encompasses behaviors which are a function of the condition of the respective syringes (i.e. synch and non-synch) of the two pump modules comprising the continuous delivery logical pump. Actual pump behavior depends on whether the pump module with the syringe which is "to be phased", i.e synch syringe, is currently the delivering pump module or not, and whether the auxiliary, i.e. second, pump module designated the non-synch syringe has enough residual capacity to carry out the phasing activity. Information as to each pump module's status is directly obtainable at the controller by calculation base on piston position data and the user's called for or commanded flow rate. In this illustrative embodiment piston position is maintained as a number of microsteps undertaken by the drive motor actuating the piston in a direction relative to a reference position (a "home" position).

Figure 2:
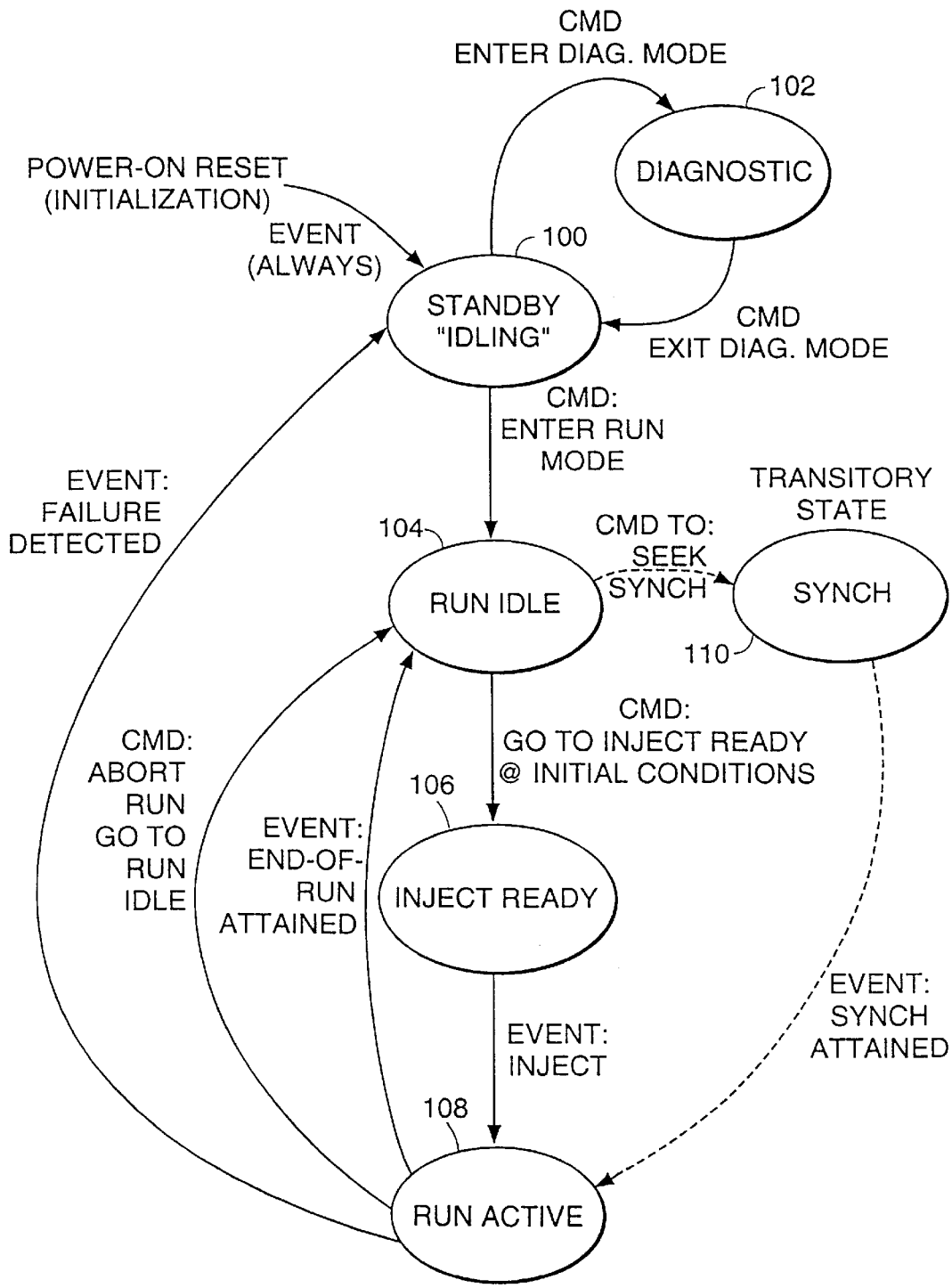
FIG. 2 is a state diagram of system operational states in a system incorporating active phasing according to the invention.

Active synchronization according to the invention, in this illustrative embodiment, is effected by a supervisory control program running on the control microprocessor. FIG. 2 illustrates a state diagram of delivery system operation and the various events or user issued commands that determine the particular state or operational mode of the system at any point in time. User issued commands are provided to the chromatography system via a suer interface, such as graphical user interfaces as known in the art. Events are system occurrences prompted by activities in the system such as a power-on system startup or the completion of a specified operation by system hardware.

An event in the form of a power-on reset operation results in initiation of power-on self testing of critical system resources, primarily confined to the system CPU board including the control microprocessor. Successful completion of low-level tests, e.g. RAM validation, EPROM checksum, A/D converter functionality, etc. as known in the art, permits the controller to continue with initialization of remaining hardware elements in the system, including positioning the pistons of each pump module to a known position. Subsequently, the pump modules are primed for delivery.

Figure 3:
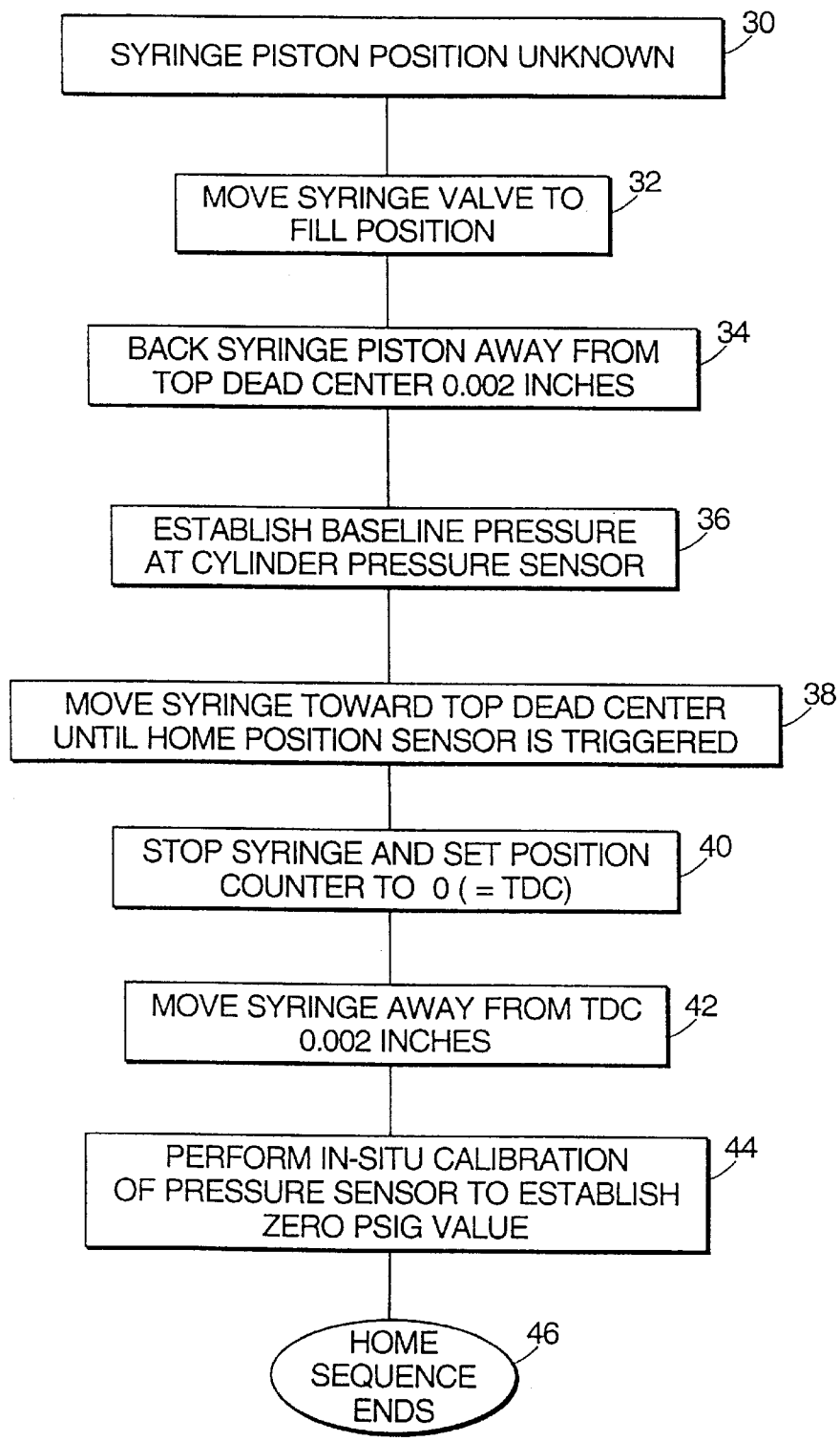
FIG. 3 is a flow diagram illustrating a process for actuating a syringe piston to a home position in a system incorporating active phasing according to the invention.

Especially relevant to active mechanical phasing according to the invention, an important initialization activity which is undertaken for each pump module in the system, prior to entering a Standby state, is the initialization to a "HOME" position, i.e. positioning the pistons of each pump module to a known position. The sequence of events used to effect HOME positioning is illustrated in FIG. 3.

The piston position of the pump modules of the logical pump is initially (theoretically) unknown 30. With the selector valve of the pump module in the "fill" position 32, the piston is actuated away from TDC (top dead center) approximately 0.002 inches 34 in order to determined a baseline pressure 36 for the cylinder via the associated pressure senor. After the piston is repositioned and the baseline pressure determined, the piston is actuated to TDC until a home position sensor is triggered 38. The piston is stopped at the home position, which is substantially equal to the TDC position, and the pump module's position counter, i.e. microstep counter, is set to zero 40. The piston is then moved away from TDC to the End-Of-Delivery position 42, which in the illustrative embodiment is removed from TDC by approximately 0.002 inches, whereat the pressure sensor can be calibrated to establish a zero pressure (i.e. 0 PSIG) value 44. At this point the home sequence is ended 46 and the actual position of the piton for each pump module is know.

The physical position of the pump module(s') mechanical elements which corresponds to HOME, can be attained with a resolution down to a single microstep of the drive motor. It should be appreciated that once HOME is attained during system power-up, all subsequent positioning of the pump module pistons is done by digital step counting. The HOME positioning sequence (as described with respect to FIG. 3) is normally only performed during power-up initialization and will not be performed again unless power is interrupted or system conditions occur which require complete initialization (e.g. piston position error).

Figure 4:
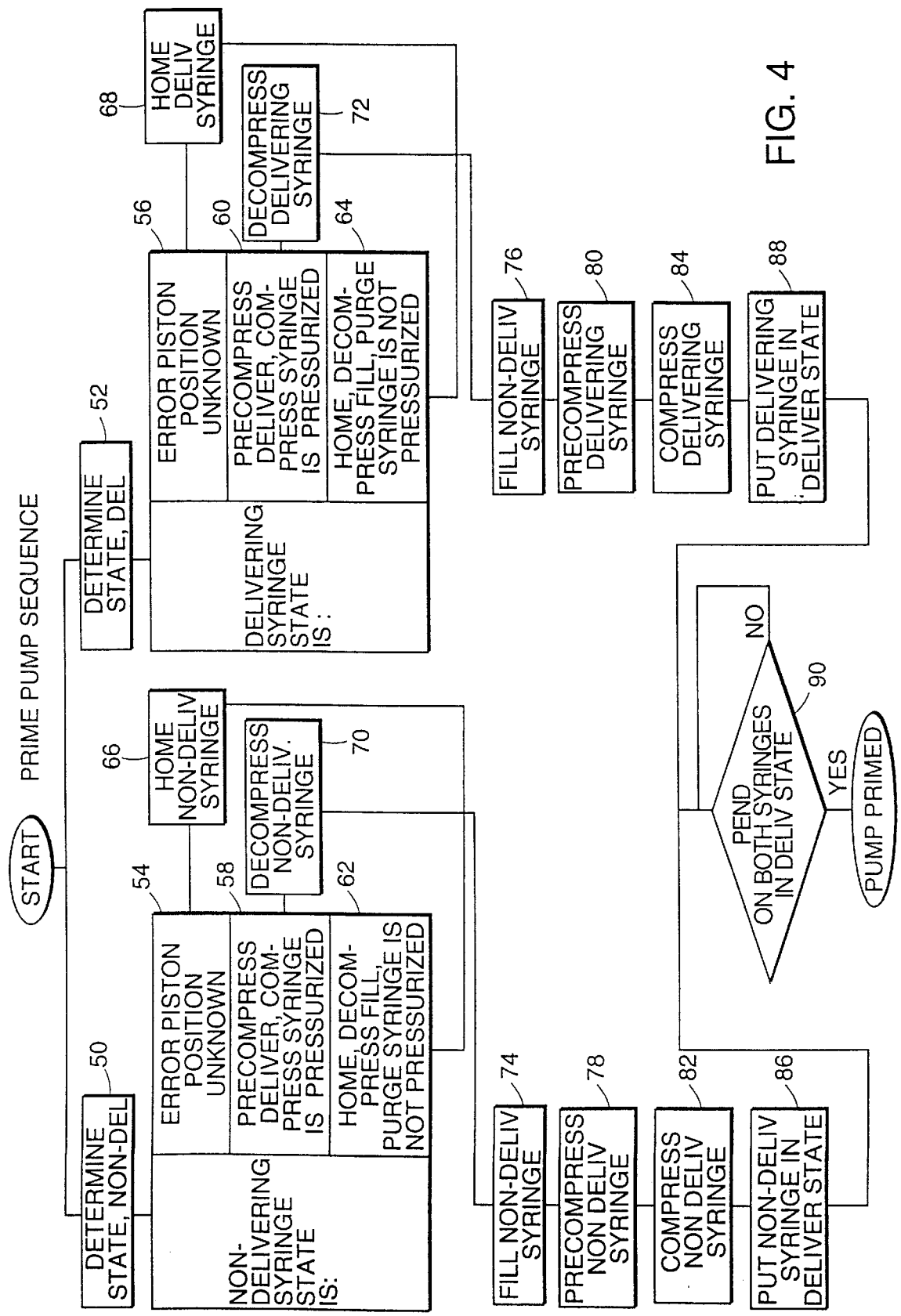
FIG. 4 is a flow diagram illustrating a process for priming a pump in a system incorporating active phasing according to the invention.

Pump priming is another important initialization undertaking that occurs prior to entry into any chromatography run state. The pump priming sequence is illustrated in FIG. 4. The priming sequence is started by determining, substantially simultaneously, the status of a non-delivering pump module 50 and the status of a delivering pump module 52 of the same logical pump. The respective status of each of the pump modules (i.e. state of the non-delivering and delivering pump modules), is one of: an error status wherein the position of the respective piston is unknown 54, 56; pressurized either precompressing, delivering or compressing 58, 60; or not pressurized, either in the HOME position, decompressing with the selector valve in the fill position, or purging 62, 64.

If the piston position of the non-delivering or delivering pump module is unknown, a known position is established 62, 64 by actuating the pump module piston(s) to the HOME position. If either pump module is in a pressurized state, the pump module should be decompressed 70, 72.

With the pistons(s) in a known position and the respective pump modules in a decompressed state, the pump module(s) can be filled 74, 76 (as described hereinafter with respect to FIG. 5), pre-compressed 78, 80, compressed to system pressure 82, 84, and put in the delivery state 86, 88. After putting the pump module(s) in the delivery state the system is set to pend 90 with both pump modules in the delivery state pending system entry into a chromatographic run mode.

Figure 5:
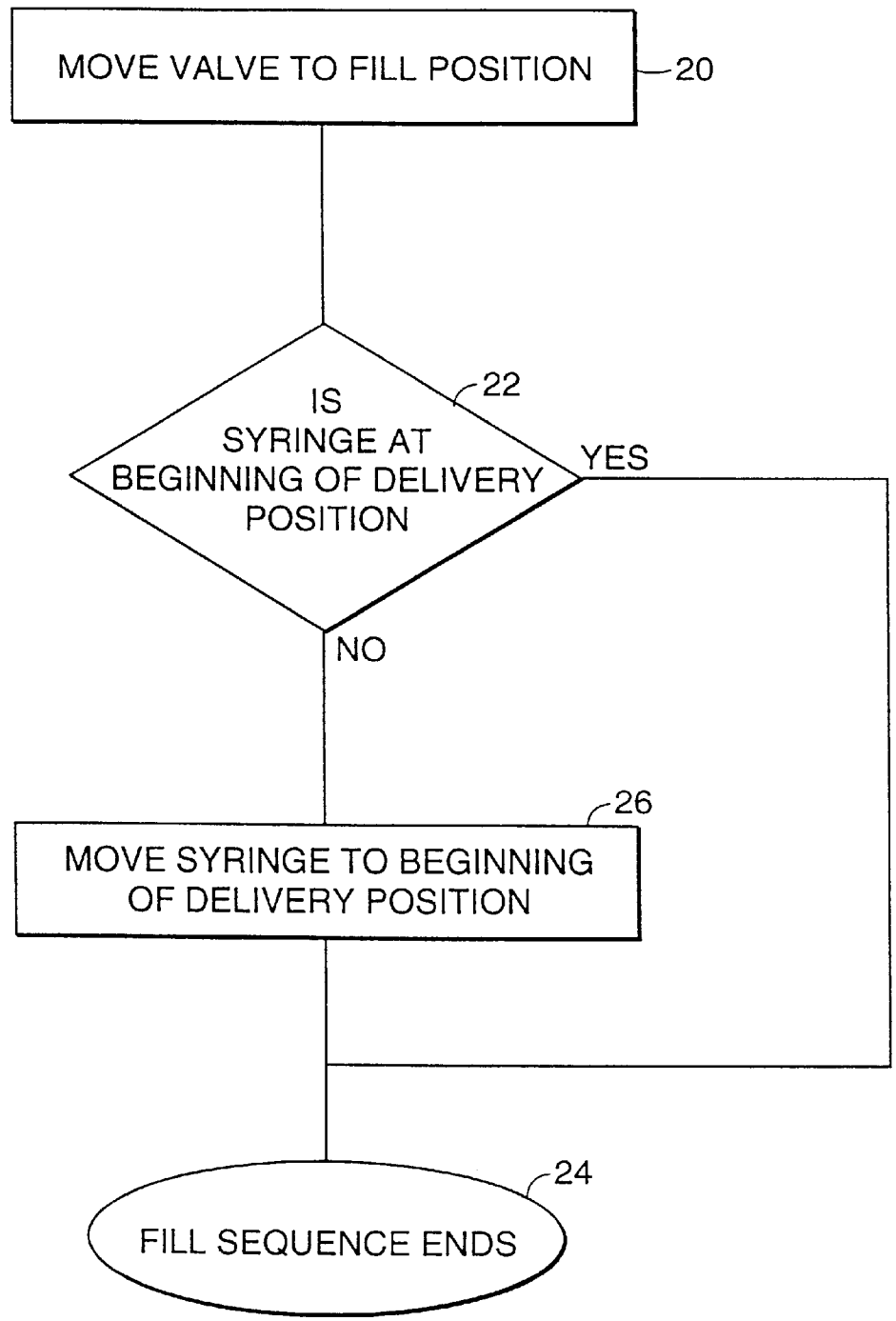
FIG. 5 is a flow diagram illustrating a process for filling a syringe in a system incorporating active phasing according to the invention.

The fill sequence, illustrated in FIG. 5, ensures that the relevant pump module has the appropriate volume of liquid require for delivery and to permit repositioning or re-phasing of the other pump module. The appropriate volume in this illustrative embodiment is the fluid volume required for regular delivery plus the volume required for exchange during the repositioning or re-phasing of the synch syringe, i.e. the complementary flow required to reposition the synch piston. The fill operation is initiated by moving the associated selector valve (18a or 18b of FIG. 1) to the fill position 20 and iteratively testing if the piston is at the beginning of the delivery position 22. The beginning of the delivery position in this illustrative embodiment is approximately 0.5 inches removed from Top Dead Center (TDC). If the piston is at the beginning of the delivery position it has the appropriate volume of liquid to effect delivery, therefore, the fill sequence ends 24. If the piston is not at the beginning of the delivery position it must be moved there 26 in order to end the fill sequence. It should be noted that the fill sequence is not only undertaken during pump priming, but is also routinely effected during the operation of the logical pump.

Once HOME is attained during system power-up, digital position counter hardware and software is initialized (i.e. zeroed-out). All further position tracking is accomplished via the incrementing and decrementing of the digital microstep count, so that there is no uncertainty introduced over time in the system representation of mechanical position. Referring again to FIG. 2, the initialization procedures terminate with a transition into the "Standby" or idling mode 100 wherein the system is powered up, not delivering any fluid. Under system control all available pump modules can be primed for delivery. The system remains in the Standby state, in which all hardware elements such as pumps, detectors and heaters are in a quiescent state, waiting for an operator to issue a command to enter a diagnostic mode 102 or a run idle mode 104.

The diagnostic mode 102 can be entered from the Standby state 100 in response to an enter diagnostic mode command. In diagnostic mode various system diagnostic can be effected to test basic system operation as will be appreciated by those skilled in the art. Upon exiting the diagnostic mode, in response to an exit diagnostic mode command, the system returns to the Standby mode 100.

The run idle mode 104 can be entered from the Standby state 100 in response to a suer issued command to enter a run mode. The run idle mode 104 is one of several modes that the system can be in when undertaking a chromatography run. In run idle mode there is no actual chromatography run data being generated or collected, however the system is at its initial conditions in accordance with the operating parameters specified by the user, including initial flow, composition, column temperature, etc. This run idle state is maintained for some selected period to permit the chromatography column to become equilibrated to the specified conditions so as to avoid transients associated with a new set of operating parameters, e.g. new composition, flow rate etc.

It should be appreciated that in the run idle state 104, run conditions can have been set as a result of a loop around from the end of a previous run, in which case the run conditions are the same conditions that were in effect at the end of the previous run. Typically, users will construct gradient profiles so that the final conditions are the same as the initial conditions (i.e. initial conditions are automatically restored at the end of a gradient run), so that the looping behavior operates very predictably. Alternatively, the run idle mode can be entered for the first time after a system power-up, in which case the user specifies, via the user interface, what initial system conditions will be in effect. In either case, the pump priming sequence must have been successfully completed in order to enable a transition to the run idle state.

When the column is equilibrated in the run idle state 104 and available for stable operation, the system can be commanded to enter the inject ready state 106. Inject ready is a state wherein the system is waiting for an inject event triggered manually or by an automatic injector as known in the art. Occurrence of the inject event causes the system to go into a run active state 108. It should be appreciated that the inject event that causes a transition from the inject ready state 106 to the run active state 108 is not synchronous with any particular mechanical event, that is, the run active state 108 entered through the inject ready state 106 does not utilize active pump phasing, i.e. pump synchronization according to the invention.

During the run active state 108 a run timer is running as the chromatography run is actually being effected. If the apparatus is being operated in a gradient mode, the gradient is executed during the run active state. Chromatography data is collected and any times events in the chromatography run specified by the operator are undertaken. In the run active state 108 a chromatogram is generated. The chromatography run in this illustrative embodiment is terminated by one of: an end of run event indicating that the chromatogram ran to completion, in which case the system returns to the run idle state 104; an abort run command issued by the operator (e.g. in a situation where the date being obtained is indicative of an unstable condition in the apparatus), in which case the system returns to the run idle state 104; and a hard failure event detected by system hardware indicating some system failure, in which case the system returns to the Standby state 100.

According to the invention, the system can transition from the run idle state 104 to the run active state 108 through a transitory synch state 110. The synch state 110 implements active phasing according to the invention. Pump synchronization is requested by an operator via the user interface in order to effect active pump phasing. By entering the transitory synch state 110 the inject ready state 106 which waits for an a synchronous inject event is avoided. The transitory synch state generates a synchronous event from which a chromatographic run is triggered. That is, the timing of a chromatographic run, i.e. the start of the run timer, is dictated by the synchronization of the pumps in the delivery system (as opposed to being dictated by an external event such as a manual or automated inject event).

The pair of pump modules comprising the logical pump and having respective syringes synchronized for continuous delivery according to the invention are arbitrarily designated as including a "synch" syringe and a "non-synch" syringe. In this illustrative embodiment a loser numbered or leftmost pump module is initially designated as being the synch syringe. It should be noted that the designation of "synch" and "non-synch" syringe will change during the execution of a run which requires multiple strokes. That is, in multiple stroke runs, synch is effected on each subsequent transition of delivery from one pump module to the other. The synch syringe will be actuated to a synch position according to the invention, i.e. a known or standardized position illustrated in FIG. 7, from which it will be the delivering syringe when fluid flow in a chromatographic run is initiated, in order to ensure substantially consistent mechanical and hydraulic performance of the system from run to run. The other syringe, designated the non-synch syringe (also referred to herein as an "auxiliary" syringe or pump module), will operate in synchronization with the synch syringe to effect continuous delivery. The other syringe, which begins the initial run as the auxiliary syringe will become the synch syringe in the subsequent stroke of a multiple stroke run, i.e. it too will be the delivering syringe beginning its delivery from a known or standardized position in order to ensure substantially consistent mechanical and hydraulic performance. This alternation can proceed over an arbitrarily large number of successive strokes.

Figure 6B:
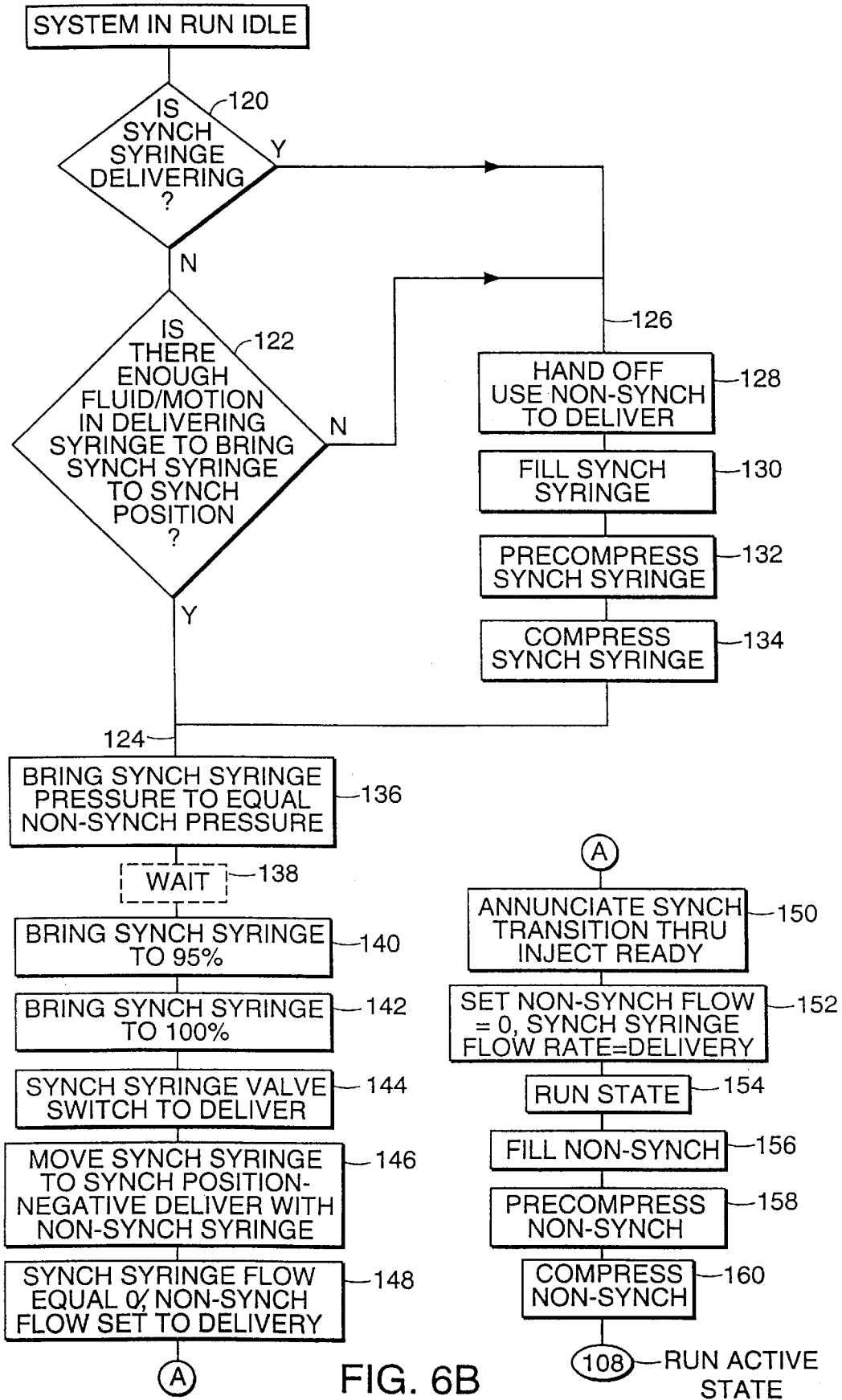
FIG. 6B is a flow diagram illustrating mechanical steps associated with active phasing according to the invention.
Figure 7:
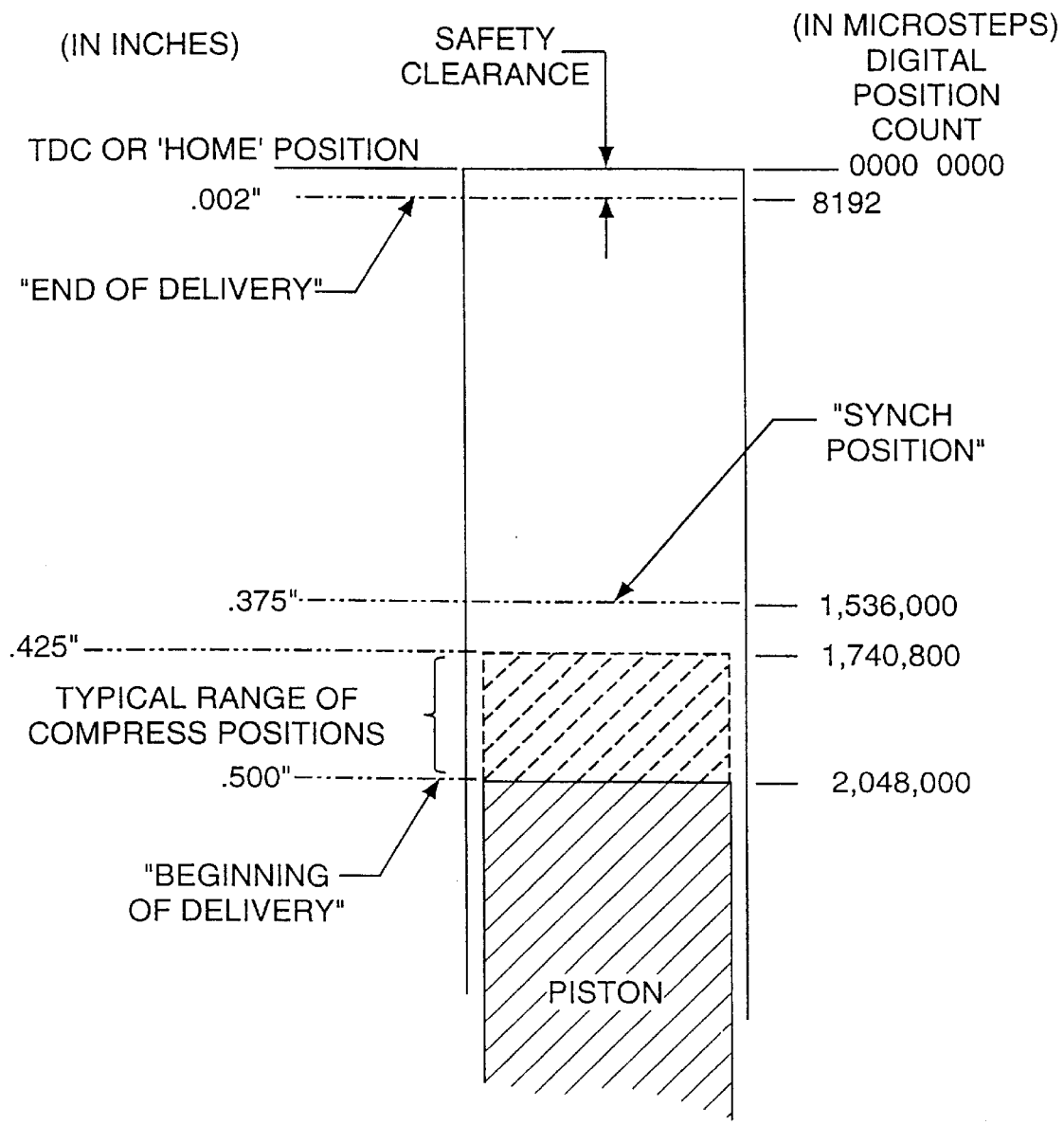
FIG. 7 is a diagrammatic illustration of syringe positions in a synch syringe.

The pump synchronization operations effected to undertake active phasing according to the invention are illustrated in FIGS. 6A and 6B. Generally, if the auxiliary pump module is delivering, and it has the required fluid capacity, the passing sequence is the shortest and simplest. In this case, the syringe to be phased (i.e. the synch syringe) is stepped through the sequence of fill, pre-compress, and compress states, until it is at the instantaneous system pressure. Then, its isolation valve is switched to bring that (synch) syringe on-line. At that point, the syringe to be phased can be repositioned under loaded, while the auxiliary syringe delivery the called-for system flow plus the flow required to compensate for any potential change in flow that would result from movement of the synch syringe to the synch position.

Advantageously, mechanical backlash is taken up in the correct direction in that the (synch) syringe to be phased is repositioned under load. Piston velocity ramping is effected as known in the art in a manner such that flow fluctuations are avoided. It should also be appreciated that in order to effect active phasing as described herein, the valves used to effect functionality as described in the referenced patent must allow for bi-directional fluid flow (i.e. both into and out of the cylinder with respect to the system).

When a target digital position count is achieved indicating the proper position (referred to as "synch" or "synch position"), the syringe "to be phased" (i.e. synch syringe) is stopped, the system controlled is notified, and the synch syringe is maintained at the position pending further commands by the system controller in accordance with system operational states (as discussed with respect to FIG. 5). if there are a plurality of logical pumps in the system, the synch piston for each pump is maintained in the synch position until the system controller is notified by all other active pumps that they have achieved starting phase or synch. In this illustrative embodiment, the synch position is a position whereat the piston is one quarter of the way into it full stroke. That is, at the synch position three quarters of a chamber of fluid is available for delivery to the receiving system.

From the synch position all active pumps can be commanded to begin execution of the run, with the result that the phased syringe of each pump, (which is on-line, and at system pressure) becomes the delivering syringe, and the previously delivering syringe goes off-line to refill, pre-pressurize, and await its next operation. Thus the synch position provides a known starting position that substantially eliminates the variability of the mechanical signature of the pump across chromatographic runs.

If there is insufficient volume available in the auxiliary syringe, or if the (synch) syringe "to be phased" is actually delivering, there are some mechanical states which must be transversed prior to beginning the "short" sequence generally discussed hereinbefore and described more particularly hereinafter with respect to FIGS. 6A and 6B. If the auxiliary syringe is delivering, but has insufficient volume to carry out the short sequence, then a hand-off to the to-be-phased (synch) syringe to performed, such that the auxiliary syringe can be taken off-line, refilled, pre-compressed, compressed to system pressure, and brought on-line again with full capacity to initiate the short sequence. Likewise, if the to-be-phased (synch) syringe is currently delivering when a phasing action is initiated, the auxiliary syringe, which is operating somewhere within the sequence of refill, pre-compress, or compress, will be allowed to complete its operation and go into the delivery state. At such a point, the auxiliary syringe has the necessary capacity and the short sequence can be initiated and completed.

More specifically, referring now to FIGS. 6A and 6B, from the run idle mode 104 the operator can request active phasing and enter into the synch mode 110 wherein the supervisory controller oversees synchronization of the pair of syringes constituting the logical pump (as well as all other logical pumps that may be present in a system).

When the system is in the run idle state, the pair of syringes, i.e. the synch syringe and the non-synch syringe can be in one of four possible conditions, as illustrated in the table of FIG. 6A. As generally described hereinbefore, the condition that the syringes are in dictates the extend of the mechanical steps that must be performed to effect synchronization. The primary considerations that are tested in the synchronization process (illustrated in FIG. 6B) and which determine the condition of the syringes and ultimately the number of steps in the synchronization procedure, are whether or not the synch syringe is in the process of delivering fluid 120 (i.e. is it on-line or off-line), and if the synch syringe is off-line the amount of fluid/travel remaining in the non-synch syringe 122 and available for delivery.

A relatively short synch procedure 124 can be effected if the present state of the synch syringe is that it is in a compress or precompress position while the nonsynch syringe is delivering and has enough remaining capacity to effect delivery without interrupting output flow while the synch syringe is actuated to the synch position. In all other cases, i.e.: when the synch syringe is in a compress/precompress position and the non-synch syringe is delivering and has insufficient capacity to effect delivery without interrupting output flow while the synch syringe is actuated to the synch position; when the synch syringe is delivering and the non-synch syringe is in a compress/precompress position; and when the synch syringe is delivering and the non-synch syringe is delivering (i.e. during handoff), a long synch procedure 126 must be effected.

The long synch procedure 126 accommodates the completion of a cycle and restoration of the synch syringe. That is, a handoff is undertaken 128 and the non-synch syringe is used for delivery while the synch syringe is taken off-line. The synch syringe is then filled 130 in accordance with the procedure described hereinbefore, and moved to a precompress position 132, which in this illustrative embodiment is 100 PSIG. The precompress position and corresponding pressure is somewhat arbitrarily chosen as a pressure to which the syringe can be taken in order to check the integrity of the mechanical elements, i.e. to check for system leaks or problems that would preclude bringing the syringe up to system pressure. The syringe is then fully compressed 134 up to a point that is substantially the system operating pressure. The synch syringe has thus been cycled and is ready to be actuated to the synch position.

The relatively short synch procedure 124 follows the long procedure 126 and facilitates fine tuning of the synch syringe once it is substantially at or near system pressure. The synch syringe, at this point in a non-delivering or off-line state, is fine turned to the desired system delivery pressure by first bringing the synch syringe pressure to a value substantially equal to the non-synch or delivering syringe pressure 136. It may be desirable to optionally wait 138 for a predefined period after bringing the synch syringe equal to the delivering syringe, so that the piston seal(s) are permitted to relax prior to bringing the synch syringe fully up to system pressure.

The synch syringe is gradually brought fully up to system pressure by first bringing it up to 95% of the delivering syringe (non-synch) pressure 140 and then up to 100% of the non-synch syringe (delivering syringe) pressure. The gradual pressurization of the synch syringe further ensures that perturbations of the delivery flow will be avoided when the synch syringe effects it delivery.

At this point, the synch syringe is ready to be brought on-line by effecting a switching of the non-delivering or synch syringe selector valve (18a, FIG. 1) to the deliver position. The valve is switched from isolation or off-line to the delivery position wherein there is system connection 144, however the flow rate out of the synch syringe is zero in that the piston is initially not actuated to drive fluid out of the syringe.

Both syringes are put on-line in order to operate in synchronization. The synch syringe is actuated, in this illustrative embodiment in the delivery direction, to the synch position (from a compress position). Such actuation of the synch syringe to the synch position temporarily introduces a flow into the receiving system which, if uncompensated, would affect (i.e. increase) the net flow delivered by the logical pump to the receiving system. If the receiving system demand (i.e. the user's commanded flow rate) from the logical pump is less than the flow rate generated by the motion of the synch syringe moving to the synch position, then the non-synch syringe will effect a compensation delivery in the form of a negative delivery operation 146 to compensate for this temporary excess of flow. thereby maintaining a constant net flow delivered to the receiving system. If instead the receiving system demand from that logical pump is greater than the flow rate generated by the motion of synch syringe moving to the synch position, then the non-synch syringe will compensate by reducing its flow rate while maintaining positive delivery, such that the sum of the synch syringe and the non-synch syringe derived flow rates from that logical pump is again held constant, and equal to the user's commanded flow rate. That is, if the receiving system demand from the logical pump is greater than the flow rate generated by the movement of the synch syringe to the synch position, the non-synch syringe effects compensation delivery in the form of a positive delivery of reduced magnitude during the synching operation, as opposed to the negative delivery effected when the receiving system demand from that logical pump is less than the flow rate generated by movement of the synch syringe to the synch position.

In any event, any change in the net flow to the receiving system creating a differential as compared to what is required by the receiving system while the synch syringe is actuating to the synch position must be compensated for by an adjustment to either or both of the sign and the magnitude of the flow generated by the non-synch syringe. When the synch syringe attains the synch position, the synch syringe flow rate is set to zero and the non-synch syringe flow rate is restored to the flow rate required for system delivery 148. If there are a plurality of pumps in the system, the syringes that attain synch will be held at zero flow rate until the other pumps in the system attain synch.

At this point it is necessary to inform the operator and/or system that synchronization has been achieved, i.e. the synch syringe is in the known synch position for the start of a chromatographic run. In the present illustrative embodiment, an audible annunciator is sounded to indicated that the synch syringe is in the synch position 150. The supervisory controller can then transition through the inject ready state, ramped the non-synch syringe flow rate to zero, and ramp the synch syringe flow rate to the system delivery flow rate making the synch syringe the delivering syringe 152. Effectively, all the mechanical operations of active phasing are completed in the synch mode (110, FIG. 2) as described hereinbefore.

The supervisory controller, upon having been informed that respective synch syringes for all of a plurality of logical pumps are in the synch position, can then transition to the run active state (108, FIG. 2) wherein the synch syringe will be the delivering syringe starting from the known synch position 154. An injector, manual or automated can be slaved to the synch sequence such that the indication that the synch position has been reached by the synch syringe(s) triggers the injector and starts the run timer to commence the chromatography run with the delivery system starting at a known position with associated (known) mechanical signature and hydraulic characteristics.

The remaining steps in the sequence involve preparing the non-synch syringe for the next handoff (in which the non-synch/auxiliary syringe will be synchronized, i.e. become the synch syringe). With the chromatography run commenced and the synch syringe providing delivery, the pump module with the non-synch syringe if off-line. For a subsequent handoff, the non-synch syringe must be filled 156, precompressed 158 and compressed to system pressure 160. At this point the system remains in the run active state (FIG. 2, 108) during the chromatography run.

It should be appreciated that while active pump phasing is implemented as described herein so that all participating pumps in an overall system are brought into known phase collectively, there is no need, after a run has commenced, to perform further actions based on collective logical pump state. That is, once any logical pump is triggered to run from a known initial mechanical phase/position, at a called for flow rate or pattern of flow rates, maintenance of various pump motions over time is accomplished according to time based system control inputs and without reference to other pumps in the system.

Although gradual pressure build-up and a wait state are described herein before with respect to bringing the synch syringe up to delivery conditions, i.e. it involves first bringing it up to 95% of the delivering syringe pressure and then up to 100% of the delivering syringe pressure, it should be appreciated that other gradations of pressure increase can be implemented, or that a slow, continuous pressure increase could be implemented with or without a substantial wait period.

Although upon reaching synch position the disclosed embodiment sounds an audible annunciator, it will be appreciated that other than an audible annunciator can be implemented to signal attainment of synch, including electrical signals of an analog or digital nature, which may be used to trigger other instrumentation such as auto injectors, timers or other associated instrumentation.

While the illustrative implementation described involves precompressing fluid in a syringe to 100 PSIG prior to compressing to system delivery pressure, it will be appreciated that other target pressures could be implemented for precompression, or precompression for checking system integrity could be undertaken only periodically or eliminated altogether.

While the invention has been shown and described herein with respect to an embodiment wherein active phasing is implemented with first and second pump modules configured as a continuous delivery (logical) pumping system, it will be appreciated that active phasing can be implemented in systems including a plurality of pump modules beyond two, and in fact may be implemented in a system to restore any number of logical pumps to a known mechanical position prior to a next run.

Similarly, while the embodiment herein is described as having pistons actuated by a microstep motor whose position is tracked by a microstep counter, it will be appreciated that alternative actuation and tracking mechanisms can be implemented, such as alternative actuation motors, for example D.C. brush or brushless motors or the like, and alternative tracking or position sensor mechanism such as position encoders or the like.

It will be appreciated that while in this illustrative embodiment the synch position is a position whereat the piston is one quarter of the way into its full stroke in order to have three quarters of a chamber of fluid available for delivery to the receiving system, such a synch position can be arbitrarily selected as any position to which an arbitrary one of a plurality of repositionable pistons can be restored prior to every run in order to substantially fix the mechanical signature and hydraulic characteristics of the pumps across plural runs.

Further, although the illustrative embodiment described herein effects a synch position by moving the piston into the cylinder, i.e. in the delivery direction, it should be appreciated that synch can be effected by moving the piston out of the cylinder in which case compensation delivery to augment flow will be substantially opposite of what is described herein.

While active phasing according to the invention is described hereinbefore implemented in the delivery system of the referenced U.S. Patent, it should be appreciated that as described, active phasing can be implemented in any of various HPLC pumping systems appropriately configured with a dedicated motor for each piston, allowing piston motion of the first piston relative to the second piston to be decoupled, independent of size or scale.

Furthermore, although the embodiment described herein is implemented in an illustrative apparatus effecting chromatography runs in accord with a supervisory control mechanism that comprises standby, diagnostic, run idle, inject ready and run active states, it will be appreciated that other operational states can be implemented in an apparatus including a synchronization state for active pump phasing according to the invention.

While the embodiment of the invention described herein includes a selector valve that has no volumetric error in switching, i.e. a positively actuated zero switching volume valve, it will be appreciated that active phasing according to the invention can be implemented in a system incorporating other switching valves, where switching volume changes can be limited by other means.

It should be further appreciated that pump synchronization according to the invention can be applied to systems where solvent compositions are formed on the low pressure, or inlet, side of the pump, for example pump synchronization can be applied in low pressure gradient formation or low pressure solvent proportioning systems, as known in the art.

Although the invention has been shown and described with respect to exemplary embodiments thereof, various other changes, omissions and additions in the form and detail thereof may be made therein without departing from the spirit and scope of the invention.

What is claimed is:

1. A fluid delivery system for continuously delivering fluid to a receiving system in accordance with a commanded volume and flow rate, comprising:

a pumping system including a first pump module and a second pump module, said first pump module including a first syringe having a first pump chamber and a first piston and said second pump module including a second syringe having a second pump chamber and a second piston;

a controller controlling said pumping system to deliver said fluid to said receiving system with said first pump module by initially moving said first piston to a known synch position whereat a selected volume of said fluid is at a selected pressure, said controller further controlling delivery of said fluid from said first pump module by providing a compensation delivery using said second pump module, so that a sum of said delivery from said first pump module and said delivery from said second pump module is equal to said commanded volume and flow rate of said fluid, wherein said delivery of said first pump module and said compensation delivery using said second pump module produces substantially no perturbation to composition or flow rate of said fluid being continuously delivered to said receiving system.

2. The fluid delivery system of claim 1 wherein said controller controls said pumping system by actuating each of said first piston and said second piton to a known home position to establish a reference position for all subsequent movements of said first piston and said second piston.

3. The fluid delivery system of claim 2 wherein said first piston and said second piston are each driven by respective microstep motors, and position of each of said first piston and said second piston is tracked by a microstep counter.

4. The fluid delivery system of claim 3 wherein said known home position is represented as a zero count of said microstep counter.

5. The fluid delivery system of claim 2 wherein said known home position is substantially equal to a top dead center position of each of said first piston and said second piston in said first pump chamber and said second pump chamber respectively.

6. The fluid delivery system of claim 1 wherein said known synch position is a position that is distal to top dead center of each of said first pump chamber and said second pump chamber in a direction opposite of delivery of fluid from each of said chambers.

7. The fluid delivery system of claim 1 wherein said controller implements a state machine effecting various states including, a power-up initialization state wherein said first piston and said second piston are positioned to known home position and wherein each of said first and second pump module is primed by filling each of said first pump chamber and said second pump chamber with a selected volume of said fluid, and compressing said selected volume of fluid to a selected delivery pressure pending delivery;

an idling state wherein said fluid delivery system is pending commencement of at least one chromatography run, and is configured to effect said at lest one chromatography run at user specified operating parameters;

a synch state being a state wherein said at least one chromatography run is not initiated until one of said first piston and said second piston is actuated to a known synch position from which said at lest one chromatography run is commenced in order to substantially ensure consistent mechanical and hydraulic performance of said apparatus and delivery system from run to run; and a run active state, entered from said synch state, wherein said at lest one chromatography run is effected in accordance with said suer specified operating parameters.

8. The fluid delivery system of claim 7 wherein priming said first pump module and said second pump module involves gradually increasing pressure of fluid in the first and second pump modules while compressing said selected volume of fluid to a selected delivery pressure.

9. The fluid delivery system of claim 7 wherein said idling state is maintained until said fluid delivery system is equilibrated to said user specified operating parameters.

10. The fluid delivery system of claim 7 wherein said controller further implements an inject ready state, said inject ready state being a state wherein said apparatus awaits an inject event to trigger commencement of said at lest one chromatographic run.

11. The fluid delivery system of claim 10, wherein said inject event is triggered in said inject ready state by one of a manual inject event or an automatic inject event.

12. The fluid delivery system of claim 10 wherein said run active state is entered from one of said synch state and said inject ready state.

13. The fluid delivery system of claim 7 wherein a first run of said at least one chromatography run is not initiated until said first piston is actuated to a known synch position from which said first run commences, and a second run of said at lest one chromatography run is not initiated until said first piston is again actuated to a known synch position from which said second run commences, in order to substantially ensure consistent mechanical and hydraulic performance of said apparatus and delivery system from run to run.

* * * * *